US010004441B2

(12) United States Patent
Feldman et al.

(10) Patent No.: US 10,004,441 B2
(45) Date of Patent: *Jun. 26, 2018

(54) SELF-POWERED ANALYTE SENSOR

(71) Applicant: Abbott Diabetes Care Inc., Alameda, CA (US)

(72) Inventors: Benjamin J. Feldman, Berkeley, CA (US); Zenghe Liu, Alameda, CA (US); Tianmei Ouyang, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/351,162

(22) Filed: Nov. 14, 2016

(65) Prior Publication Data
US 2017/0188904 A1 Jul. 6, 2017

Related U.S. Application Data

(63) Continuation of application No. 12/717,634, filed on Mar. 4, 2010, which is a continuation of application
(Continued)

(51) Int. Cl.
*A61B 5/1486* (2006.01)
*A61B 5/00* (2006.01)
(Continued)

(52) U.S. Cl.
CPC .......... *A61B 5/1486* (2013.01); *A61B 5/0004* (2013.01); *A61B 5/14532* (2013.01);
(Continued)

(58) Field of Classification Search
CPC ..... A61B 5/1486; A61B 5/0004; A61B 90/98; A61B 5/6849; A61B 5/14532; G01N 27/3273; G01N 27/3274; C12Q 1/006
See application file for complete search history.

(56) References Cited

U.S. PATENT DOCUMENTS 5,437,999 A * 8/1995 Diebold ................. C12Q 1/001
204/403.11
5,667,653 A * 9/1997 Schneider ............ G01N 27/404
204/400
(Continued)

OTHER PUBLICATIONS

Kakehi N. et al: "A Novel Wireless Glucose Sensor Employing Direct Electron Transfer Principle Based Enzyme Fuel Cell", Biosensors and Bioelectronics, vol. 22, Jan. 1, 2007, pp. 2250-2255.
(Continued)

*Primary Examiner* — Meredith Weare
(74) *Attorney, Agent, or Firm* — Arent Fox LLP

(57) ABSTRACT

Generally, embodiments of the invention relate to self-powered analyte determining devices (e.g., electrochemical analyte monitoring systems) that include a working electrode, a counter electrode, and an optional resistance value, where the working electrode includes analyte sensing components and the self-powered analyte determining device spontaneously passes a current directly proportional to analyte concentration in the absence of an external power source. Also provided are systems and methods of using the, for example electrochemical, analyte sensors in analyte monitoring.

24 Claims, 14 Drawing Sheets

Related U.S. Application Data

No. 12/393,921, filed on Feb. 26, 2009, now abandoned.

(51) Int. Cl.
*A61B 90/98* (2016.01)
*A61B 5/145* (2006.01)
*G01N 27/327* (2006.01)
*C12Q 1/00* (2006.01)

(52) U.S. Cl.
CPC ............ *A61B 5/6849* (2013.01); *A61B 90/98* (2016.02); *C12Q 1/006* (2013.01); *G01N 27/3273* (2013.01); *G01N 27/3274* (2013.01)

(56) References Cited

U.S. PATENT DOCUMENTS

| | | | | |
|---|---|---|---|---|
| 5,820,622 | A * | 10/1998 | Gross | A61K 9/0021 204/280 |
| 6,442,413 | B1 | 8/2002 | Silver | |
| 9,668,684 | B2 * | 6/2017 | Feldman | A61B 5/1486 |
| 2004/0245101 | A1 | 12/2004 | Willner et al. | |
| 2010/0213082 | A1 * | 8/2010 | Feldman | A61B 5/1486 205/777.5 |

OTHER PUBLICATIONS

Extended European Search Report issued in EP Patent Application No. 17183254.6 dated Oct. 19, 2017.

* cited by examiner

Intermittently Sampled Transcutaneous Sensors
A. Primary receiver unit is contacted directly to sensor leads as desired
B. Primary receiver unit queries RF powered circuit at regular intervals
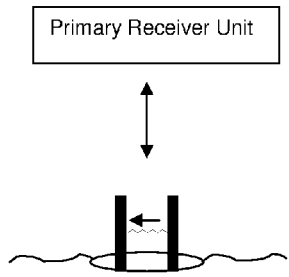
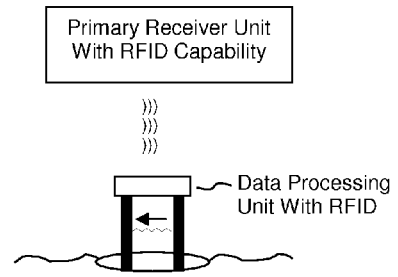
FIG. 2

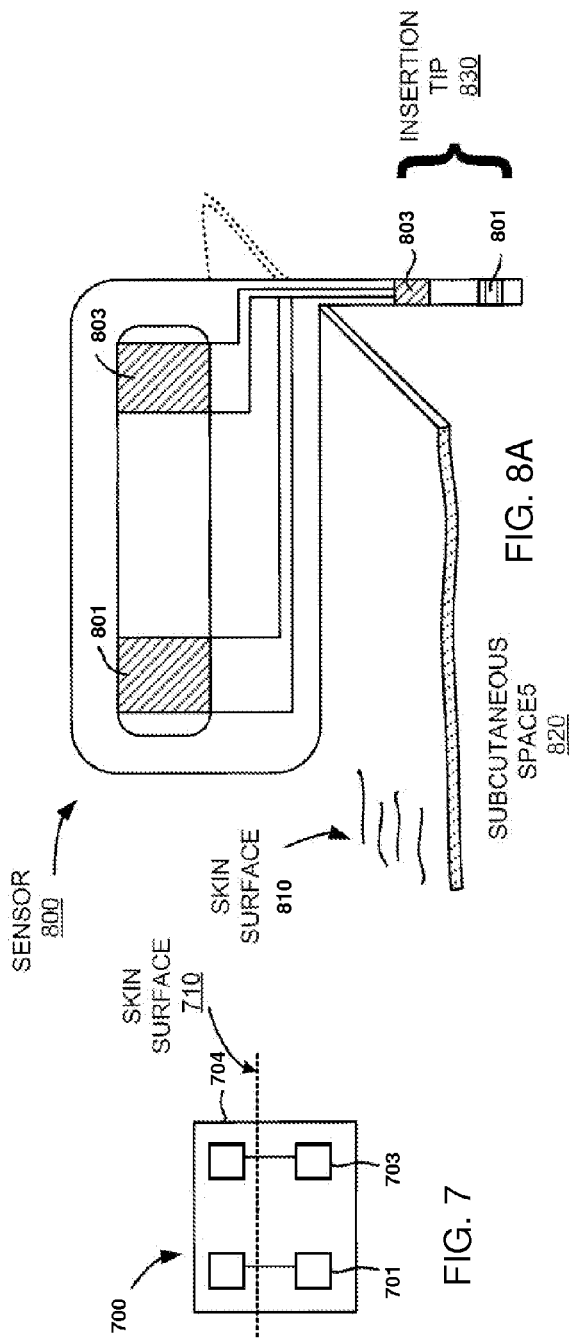

SELF-POWERED ANALYTE SENSOR

BACKGROUND OF THE INVENTION

Electronic and electromechanical systems that are implanted in the body of animals, such as sensors and their associated electronic circuits that function to amplify the sensor signals and transmit them to a nearby receiver, require a power source. Currently, these systems are powered externally by batteries. The smallest batteries are, however, much larger than the implantable sensors and their associated signal amplifier circuits. For this reason, the size of autonomous packages that include a sensor, an amplifier-transmitter, and a power source are generally defined by the battery. Batteries cannot be made as small as the sensors or amplifiers because the batteries require cases and seals, the miniaturization of which is difficult and prohibitively expensive.

Known fuel cells are also much larger than available sensors because they require a case and a seal, and usually also a membrane, which is difficult to miniaturize and seal. Biological fuel cells, also known as biofuel cells, have been described in the past fifty years. However, only a few of these biofuel cells could be operated under physiological conditions. Physiological conditions include, for instance, a pH of about 7.2 to 7.4, a temperature of near 37° C., and a chloride concentration of about 0.14 M. Furthermore, known biofuel cells having higher power densities require ion-conducting separation membranes.

Accordingly, there still exists a need for the development of a system having millimeter to sub-millimeter dimensions that can function under physiological conditions to provide power to a sensor.

SUMMARY OF THE INVENTION

Generally, embodiments of the invention relate to self-powered analyte determining devices (e.g., electrochemical analyte monitoring systems) that include a working electrode, a counter electrode, and an optional resistance value, where the working electrode includes analyte sensing components and the self-powered analyte determining device spontaneously passes a current directly proportional to analyte concentration in the absence of an external power source. Also provided are systems and methods of using the, for example electrochemical, analyte sensors in analyte monitoring.

These and other objects, advantages, and features of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 2 is a schematic illustration of an application of a self-powered analyte sensor according to an embodiment of the invention for use in transcutaneous sensing of an analyte level. Panel A shows an embodiment in which a self-powered analyte sensor is implanted transcutaneously and a hand-held display is contacted directly to sensor leads as desired to measure the current flow and calculate the analyte level. Panel B shows an embodiment in which a self-powered analyte sensor is implanted transcutaneously, where the self-powered analyte sensor is further coupled to a radio-frequency (RF) powered measurement circuit. The RF powered measurement circuit is then remotely queried at regular intervals by an RF-power equipped hand-held display in order to provide continuous analyte level measurements.

FIG. 7 shows a schematic diagram of an embodiment of an exemplary analyte sensor.

FIGS. 8A and 8B show a perspective view and a cross sectional view, respectively of another exemplary analyte sensor.

Figure 1:
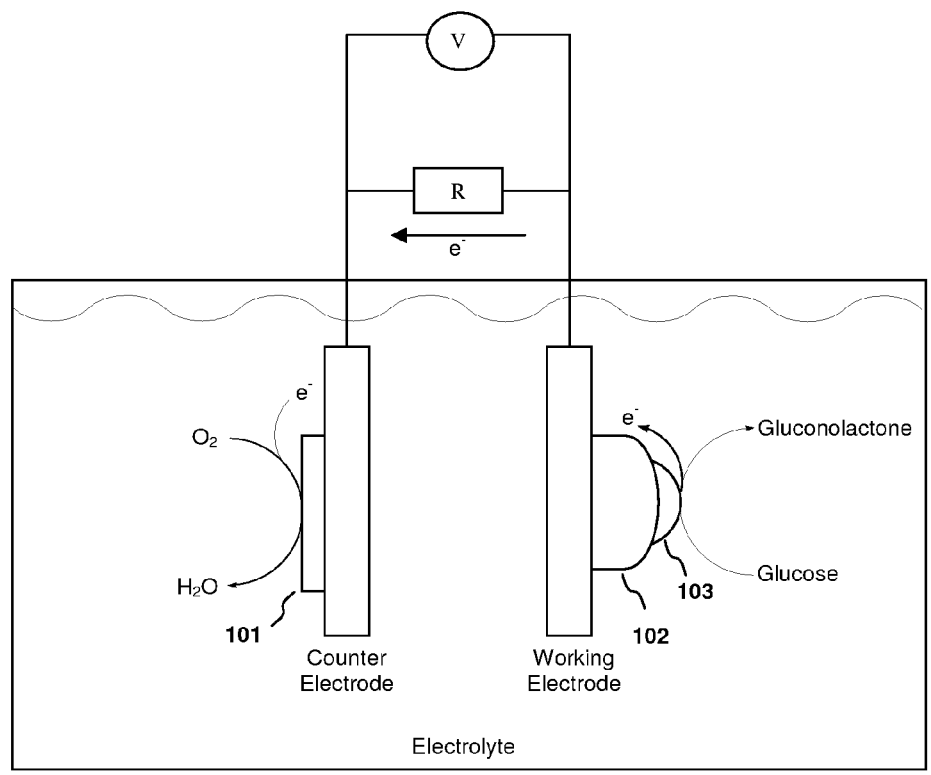
FIG. 1 is a schematic illustration of electron transfer in the electrocatalytic oxidation of glucose and in the electrocatalytic reduction of oxygen that occurs in a self-powered analyte sensor according to an embodiment of the invention.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Generally, embodiments of the invention relate to self-powered analyte determining devices (e.g., electrochemical analyte monitoring systems) that include a working electrode, a counter electrode, and an optional resistance value, where the working electrode includes analyte sensing components and the self-powered analyte determining device spontaneously passes a current directly proportional to analyte concentration in the absence of an external power source. Also provided are systems and methods of using the, for example electrochemical, analyte sensors in analyte monitoring.

The self-powered analyte sensor uses compounds available in a variety of biological systems to provide a low level of power and also detect a level of an analyte. In general, the self-powered analyte sensor described herein spontaneously passes a current proportional to an analyte concentration, such as glucose, in the absence of an external power supply, such as a battery. As such, a self-powered analyte sensor that is partially implanted under the skin of a subject or fully implanted under the skin of a subject can be coupled to a radio-frequency powered measurement circuit to remotely provide analyte levels.

Non-self-powered continuous analyte sensors have fairly long equilibration times, and therefore need to be continuously powered after inserting a portion thereof under the skin of a subject. That is, if the power supply of a continuous analyte sensor is removed and it is turned "off", then a fairly long wait time of approximately 10 to 15 minutes must pass before a reliable analyte level reading is detected following reconnection of the power supply. In contrast, a self-powered analyte sensor, as described herein, has the advantage of providing a low level of continuous power in the absence of an external power supply while also detecting an analyte level thereby requiring little to no equilibration time between analyte measurement intervals.

With reference to the schematic illustration of FIG. 1, during the operation of the self-powered analyte sensor, the primary reactant (e.g., reductant) is electrooxidized at the working electrode electrocatalyst layer 102 and 103 and the secondary reactant (e.g., oxidant) is electroreduced at the counter electrode electrocatalyst layer 101. The redox polymer 102 disposed on the working electrode passes electrons, or a current, between the primary reactant and the working electrode, while the electrocatalyst layer 101 disposed on the counter electrode, such as redox polymer, redox polymer with enzyme, or platinum, passes electrons, or a current to the counter electrode. The electrical power is generated from the overall oxidation or reduction of the working electrode primary reactant, such as a reductant or oxidant, by the counter electrode secondary reactant, such as oxidant or reductant. In a biological system, for example, the electrical power can be generated by the overall oxidation of glucose, lactate, or pyruvate by dissolved oxygen, delivered as, for example, hemoglobin-bound oxygen ($HbO_2$), which is in rapid equilibrium with dissolved oxygen passing through the oxygen-permeable membranes of red blood cells. The self-powered analyte sensor facilitates this oxidation reaction, and uses the resulting flow of electrons to produce an electrical current that provides a low-level of power. The electrocatalyst layer of the working electrode is involved in generating the low-level of power and also functions as the sensing layer that is involved in analyte-level detection, thereby providing the dual-function of power generation and analyte level detection.

In one embodiment of the invention, an enzyme used for the electrooxidation of glucose can be GOx disposed on the working electrode with redox polymer and cross-linker, and the electrocatalyst for the electroreduction of oxygen can be redox polymer, redox polymer with enzyme, or platinum-carbon cloth disposed on the counter electrode. In the operation of the cell, via its wiring, electrons are collected from glucose-reduced GOx at the working electrode, where glucose is electrooxidized to δ-gluconolactone (see Eq. 1 below), and electrons are delivered to the reox polymer, redox polymer with enzyme, or platinum-carbon cloth at the counter electrode, where oxygen is electroreduced to water (see Eq. 2 below). The overall reaction is that of Eq. 3 below.

$$D\text{-glucose} \rightarrow \delta\text{-gluconolactone} + 2H^+ + 2e^- \quad \text{(Eq. 1)}$$

$$O_2 + 4H^+ + 4e^- \rightarrow 2H_2O \quad \text{(Eq. 2)}$$

$$2D\text{-glucose} + O_2 \rightarrow 2\delta\text{-gluconolactone} + 2H_2O \quad \text{(Eq. 3)}$$

The reactions represented by Eqs. 1-3 above are now described in relation to the schematic illustration of FIG. 1. FIG. 1 illustrates the electron transfer involved in the electrocatalytic oxidation of glucose and the electron transfer involved in the electrocatalytic reduction of oxygen. In the self-powered analyte sensor, the working electrode and the counter electrode reside in the same solution or same compartment. As shown, electrons are first transmitted from a glucose molecule to an enzyme, such as GOx merely by way of illustration. Glucose is therefore electrooxidized to form a gluconolactone molecule, and enzyme is reduced. Protons are generally released into the biological system via this reaction (see Eq. 1), while the captured electrons are transmitted to the working electrode through a redox polymer, such as an osmium(Os)-complex-based redox polymer, disposed on the working electrode. The electrons then travel from the working electrode to an electrical circuit to provide a low level of power. The electrons eventually make their way to the counter electrode via an optional resistor having an R value, where they are transmitted through an electrocatalyst layer, such as an Os-complex-based redox polymer merely by way of illustration, disposed on the counter electrode. The electrons are then passed on to an oxygen molecule in the biological system, which captures both the transmitted electrons and protons from the biological system to form a water molecule.

A working electrode of the self-powered analyte sensor effectuates the electrooxidation of the reductant, such as the electrooxidation of glucose to gluconolactone as schematically illustrated in FIG. 1. As described previously, enzymes, examples of which are oxidases and dehydrogenases, disposed on the working electrode catalyze this electrooxidation of the reductant, such as glucose. These enzymes are wired to the working electrode via a redox polymer disposed proximate to the enzyme and the working electrode. An example of a redox polymer is a polymer derived from the copolymer of poly(acrylamide) and poly(4-vinyl pyridine) and including an Os complex. Another example of a redox polymer is a redox polymer derived from poly(N-vinyl imidazole) and including an Os complex. In these examples, the Os(II) and Os(III) centers of the redox polymers and the enzymes are immobilized in electron-conducting films on the surfaces of the working electrode.

A counter electrode of the self-powered analyte sensor effectuates the four-electron electroreduction of $O_2$ to water under physiological conditions as schematically illustrated in FIG. 1. The counter electrode can also, for example catalyze the two electrode reduction of $O_2$ to hydrogen peroxide. This electroreduction reaction is catalyzed by the electrocatalyst 101 layer disposed on the counter electrode. In some embodiments, the electrocatalyst 101 includes platinum wire, platinum black, platinum ink, or platinum impregnated carbon disposed on the counter electrode. In certain embodiments, the electrocatalyst 101 is a redox polymer disposed on the counter electrode. An example of a redox polymer of a electrocatalyst layer 101 disposed on a counter electrode is a polymer derived from the copolymer of poly(acrylamide) and poly(4-vinyl pyridine) and including an Os complex. Another example of a redox polymer is a redox polymer derived from poly(N-vinyl imidazole) and including an Os complex. In these examples, the Os(II) and Os(III) centers of the redox polymers are immobilized in electron-conducting films disposed on the surfaces of the counter electrode. In certain embodiments, enzymes such as BOD, Laccase, and the like, are complexed to the redox polymer disposed on the counter electrode. Both working and counter electrode may be overlaid by a flux-reducing biocompatible membrane, as described in the examples, below.

The physical dimensions of the self-powered analyte sensor, as well as its operational parameters (e.g., output power and voltage) are, at least in part, a function of the components that form the sensor. Merely by way of example, the voltage drop across the resistance, R, of the self-powered analyte sensor can range from about 0 volts to about 1.2 volts, and typically, from about 0 volts to about 0.3 volts.

The output current of an implanted self-powered analyte sensor, can be limited by electrode kinetics, ohmic resistance, and/or mass transport. When the electrode kinetics is fast and the self-powered analyte sensor is small enough for the ohmic resistance of the electrolytic solution to be low, the output current is determined by the mass transport of the reactants to the electrodes. In particular, output current is generally determined by mass transport of a single limiting reactant, for example glucose. The mass-transport-limited current density increases upon raising the concentration of the reactants, particularly the limiting reactant, or upon increasing the permeability of any overlying membrane.

The self-powered analyte sensor further includes an optional resistance disposed between the working electrode and the counter electrode and having an R value that is chosen from within a range of R values for which an electrochemical analyte sensor current output at an analyte concentration at the top of the physically relevant range of the analyte is independent of R. Such an R value can be calculated, as exemplified in FIG. 14, by determining the current output at a selected analyte concentration at the top of the physically relevant range of the analyte for a variety of selected R values. The R value is then determined to be the series of R values that correspond to a steady state current output from the electrochemical sensor, i.e., the rate at which the current output is stable and does not change over the varying R values. For example, in FIG. 14, the current output (solid line with diamonds) for the sensor is independent of the R value from 0 MΩ to 10 MΩ. In some embodiments, the R value is a whole integer and in other embodiments the R value is a fraction of a whole integer.

In some embodiments, the R value is chosen such that the potential drop across the resistor, at an analyte concentration at the top of its physically relevant range, is less than 75% of the open circuit potential. In other embodiments, the R value is chosen such that the potential drop across the resistor, at an analyte concentration at the top of its physically relevant range, is less than 50% of the open circuit potential. In some embodiments, the R value is chosen such that the potential drop across the resistor, at an analyte concentration at the top of its physically relevant range, is less than 25% of the open circuit potential. In certain embodiments, the R value is less than about 40 MΩ, including less than about 20 MΩ, less than about 10 MΩ, and less than about 1 MΩ, Thus, in accordance with an embodiment of the invention, the self-powered analyte sensor is usually assembled without the case, the seal, and the compartment-separating membrane required by conventional batteries. As a result, the self-powered analyte sensor can be manufactured with a footprint smaller than about 3 mm$^2$, including smaller than about 1 mm$^2$, such as smaller than about 0.3 mm$^2$. The self-powered analyte sensor, with dimensions on the millimeter to sub-millimeter level, can power sensor components, as further described herein. Further, the self-powered analyte sensor can be constructed so that none of its components, including its catalytic components, will be dissolved or leached while residing in the body.

FIG. 2 is a schematic illustration of an application of a self-powered analyte sensor according to an embodiment of the invention for use in transcutaneous sensing of an analyte level. Panel A shows an embodiment in which a self-powered analyte sensor is implanted transcutaneously and a hand-held display and primary receiver unit is contacted directly to sensor leads as desired to measure the current flow and calculate the analyte level. Panel B shows an embodiment in which a self-powered analyte sensor is implanted transcutaneously, where the self-powered analyte sensor is further coupled to a radio-frequency (RF) powered measurement circuit. The RF powered measurement circuit and data processing unit is then remotely queried at regular intervals by an RF-power equipped hand-held display and primary receiver unit in order to provide analyte level measurements. In such embodiments, the RF-powered equipped hand-held display and primary receiver unit is brought into close proximity to the transcutaneously implanted sensor at regular intervals. In some embodiments, the radio-frequency powered current measuring circuit and data processing unit is intermittently powered. In some embodiments, the sensor is coupled to an inductively powered current measuring circuit and data processing unit. In certain embodiments, the inductively powered current measuring circuit and data processing unit is intermittently powered.

Figure 3:
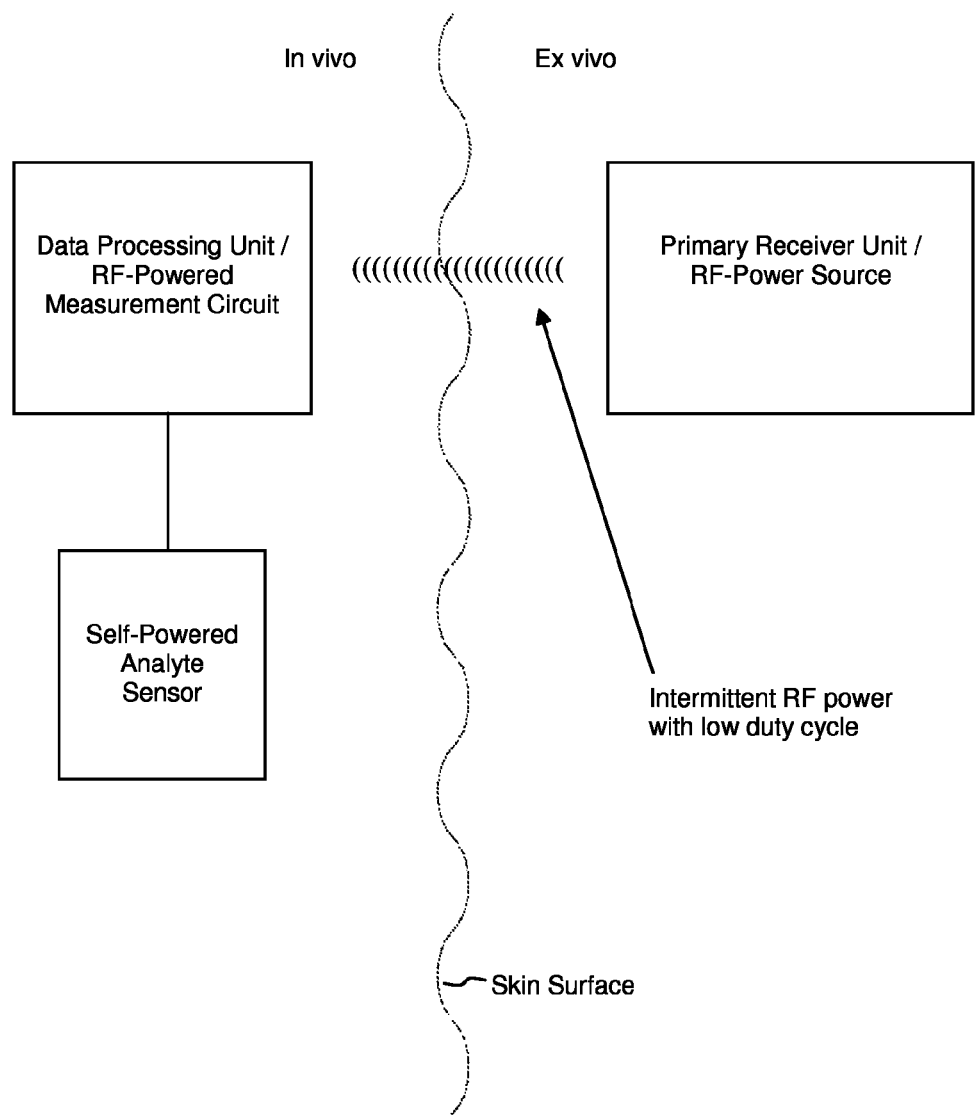
FIG. 3 is a schematic illustration of a fully implanted self-powered analyte sensor coupled to a radio-frequency (RF)-powered measurement circuit that may be intermittently RF-powered with an external RF-power source when an analyte measurement is desired. As a result, the RF-power source may be moved away from the site of implantation of the self-powered analyte sensor at any time and no re-equilibration period is required when it is brought back into RF communication with the site of implantation.

FIG. 3 is a schematic illustration of a fully implanted self-powered analyte sensor coupled to a radio-frequency (RF)-powered potentiostat measurement circuit and data processing unit that may be intermittently RF-powered with an external RF-power source when an analyte measurement is desired. In such embodiments, the RF-powered potentiostat measurement circuit and data processing unit is brought into close proximity to the implanted sensor at regular intervals. As a result, the RF-power source may be moved away from the site of implantation of the self-powered analyte sensor at any time and no re-equilibration period is required when it is brought back into RF communication with the site of implantation. In some embodiments, the radio-frequency powered current measuring circuit and data processing unit is intermittently powered. In some embodiments, the sensor is coupled to an inductively powered current measuring circuit and data processing unit. In certain embodiments, the inductively powered current measuring circuit and data processing unit is intermittently powered.

Electrochemical Sensors

Embodiments of the invention relate to methods and devices for detecting at least one analyte, including glucose, in body fluid. Embodiments relate to the continuous and/or automatic in vivo monitoring of the level of one or more analytes using a continuous analyte monitoring system that includes an analyte sensor at least a portion of which is to be positioned beneath a skin surface of a user for a period of time and/or the discrete monitoring of one or more analytes using an in vitro blood glucose ("BG") meter and an analyte test strip. Embodiments include combined or combinable devices, systems and methods and/or transferring data between an in vivo continuous system and an in vivo system. In some embodiments, the systems, or at least a portion of the systems, are integrated into a single unit.

A self-powered analyte sensor may be an in vivo sensor or an in vitro sensor (i.e., a discrete monitoring test strip). Such a sensor can be formed on a substrate, e.g., a substantially planar substrate. In certain embodiments, such a sensor is a wire, e.g., a working electrode wire inner portion with one or more other electrodes associated (e.g., on, including wrapped around) therewith. The sensor also includes at least one counter electrode.

Accordingly, embodiments include self-powered analyte monitoring devices and systems that include an analyte sensor at least a portion of which is positionable beneath the skin of the user for the in vivo detection, of an analyte, including glucose, lactate, and the like, in a body fluid. Embodiments include wholly implantable self-powered analyte sensors and analyte sensors in which only a portion of the sensor is positioned under the skin and a portion of the sensor resides above the skin, e.g., for contact to a sensor control unit (which may include a transmitter), a receiver/display unit, transceiver, processor, etc. The sensor may be, for example, subcutaneously positionable in a patient for the continuous or periodic monitoring of a level of an analyte in a patient's interstitial fluid. For the purposes of this description, continuous monitoring and periodic monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Self-powered analyte sensors may be insertable into a vein, artery, or other portion of the body containing fluid. Embodiments of the analyte sensors of the subject invention having a plasticizer may be configured for monitoring the level of the analyte over a time period which may range from seconds, minutes, hours, days, weeks, to months, or longer.

Of interest are self-powered analyte sensors, such as glucose sensors, that are capable of in vivo detection of an analyte for about one hour or more, e.g., about a few hours or more, e.g., about a few days or more, e.g., about three or more days, e.g., about five days or more, e.g., about seven days or more, e.g., about several weeks or at least one month or more. Future analyte levels may be predicted based on information obtained, e.g., the current analyte level at time t0, the rate of change of the analyte, etc. Predictive alarms may notify the user of a predicted analyte levels that may be of concern in advance of the user's analyte level reaching the future level. This provides the user an opportunity to take corrective action.

Figure 4:
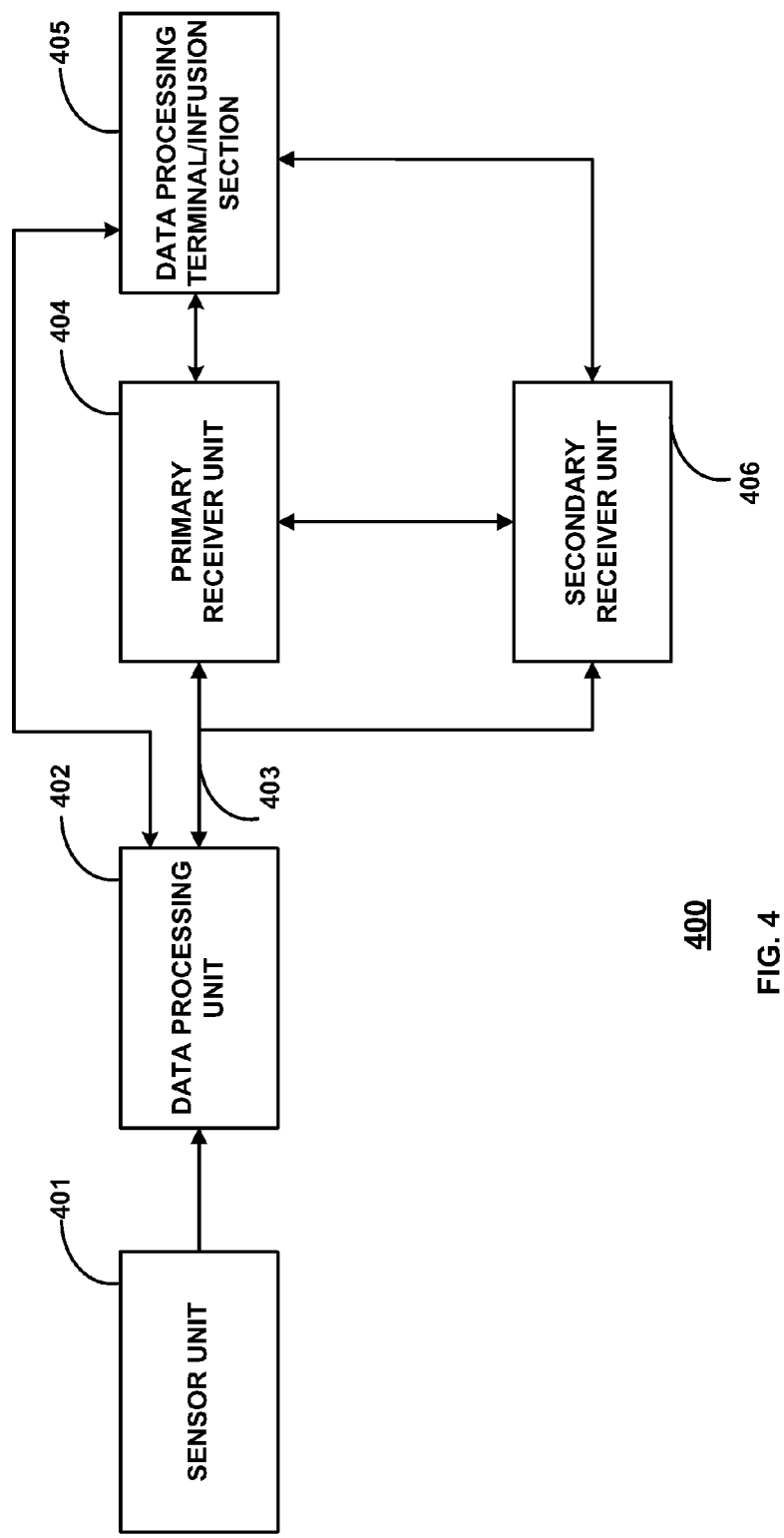
FIG. 4 shows a block diagram of an embodiment of a data monitoring and management system according to embodiments of the invention.

FIG. 4 shows a data monitoring and management system such as, for example, an analyte (e.g., glucose) monitoring system 400 in accordance with certain embodiments. Embodiments of the subject invention are further described primarily with respect to glucose monitoring devices and systems, and methods of glucose detection, for convenience only and such description is in no way intended to limit the scope of the invention. It is to be understood that the self-powered analyte monitoring system may be configured to monitor a variety of analytes at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 400 includes a sensor 401, a data processing unit 402 connectable to the sensor 401, and a primary receiver unit 404 which is configured to communicate with the data processing unit 402 via a communication link 403. In certain embodiments, the primary receiver unit 104 may be further configured to transmit data to a data processing terminal 405 to evaluate or otherwise process or format data received by the primary receiver unit 404. The data processing terminal 405 may be configured to receive data directly from the data processing unit 402 via a communication link which may optionally be configured for bi-directional communication. Further, the data processing unit 402 may include a transmitter or a transceiver to transmit and/or receive data to and/or from the primary receiver unit 404 and/or the data processing terminal 405 and/or optionally the secondary receiver unit 406.

Also shown in FIG. 4 is an optional secondary receiver unit 406 which is operatively coupled to the communication link and configured to receive data transmitted from the data processing unit 402. The secondary receiver unit 406 may be configured to communicate with the primary receiver unit 404, as well as the data processing terminal 405. The secondary receiver unit 406 may be configured for bi-directional wireless communication with each of the primary receiver unit 404 and the data processing terminal 405. As discussed in further detail below, in certain embodiments the secondary receiver unit 406 may be a de-featured receiver as compared to the primary receiver, i.e., the secondary receiver may include a limited or minimal number of functions and features as compared with the primary receiver unit 404. As such, the secondary receiver unit 406 may include a smaller (in one or more, including all, dimensions), compact housing or embodied in a device including a wrist watch, arm band, PDA, etc., for example. Alternatively, the secondary receiver unit 406 may be configured with the same or substantially similar functions and features as the primary receiver unit 404. The secondary receiver unit 406 may include a docking portion to be mated with a docking cradle unit for placement by, e.g., the bedside for night time monitoring, and/or a bi-directional communication device. A docking cradle may recharge a powers supply.

Only one self-powered sensor 401, data processing unit 402 and data processing terminal 405 are shown in the embodiment of the analyte monitoring system 400 illustrated in FIG. 4. However, it will be appreciated by one of ordinary skill in the art that the analyte monitoring system 400 may include more than one sensor 401 and/or more than one data processing unit 402, and/or more than one data processing terminal 405. Multiple self-powered sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions. In certain embodiments, a first sensor may be used to calibrate a second sensor.

The analyte monitoring system 400 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 400. For example, unique IDs, communication channels, and the like, may be used.

In certain embodiments, the sensor 401 is physically positioned in or on the body of a user whose analyte level is being monitored. The sensor 401 may be configured to at least periodically sample the analyte level of the user and convert the sampled analyte level into a corresponding signal for transmission by the data processing unit 402. The data processing unit 402 is coupleable to the self-powered sensor 401 so that both devices are positioned in or on the user's body, with at least a portion of the self-powered analyte sensor 401 positioned transcutaneously. The data processing unit may include a fixation element such as adhesive or the like to secure it to the user's body. An optional mount (not shown) attachable to the user and mateable with the unit 402 may be used. For example, a mount may include an adhesive surface. The data processing unit 402 performs data processing functions, where such functions may include but are not limited to, filtering and encoding of data signals, each of which corresponds to a sampled analyte level of the user, for transmission to the primary receiver unit 404 via the communication link 403. In one embodiment, the self-powered sensor 401 or the data processing unit 402 or a combined self-powered sensor/data processing unit may be wholly implantable under the skin layer of the user.

In certain embodiments, the primary receiver unit 404 may include an analog interface section including and RF receiver and an antenna that is configured to communicate with the data processing unit 402 via the communication link 403, and a data processing section for processing the received data from the data processing unit 402 including data decoding, error detection and correction, data clock generation, data bit recovery, etc., or any combination thereof.

In operation, the primary receiver unit 404 in certain embodiments is configured to synchronize with the data processing unit 402 to uniquely identify the data processing unit 402, based on, for example, an identification information of the data processing unit 402, and thereafter, to periodically receive signals transmitted from the data processing unit 402 associated with the monitored analyte levels detected by the sensor 401.

Referring again to FIG. 4, the data processing terminal 405 may include a personal computer, a portable computer including a laptop or a handheld device (e.g., personal digital assistants (PDAs), telephone including a cellular phone (e.g., a multimedia and Internet-enabled mobile phone including an iPhone™, iPOD™ or similar phone), mp3 player, pager, and the like), drug delivery device, each of which may be configured for data communication with the receiver via a wired or a wireless connection. Additionally, the data processing terminal 405 may further be connected to a data network (not shown) for storing, retrieving, updating, and/or analyzing data corresponding to the detected analyte level of the user.

The data processing terminal 405 may include an infusion device such as an insulin infusion pump or the like, which may be configured to administer insulin to patients, and which may be configured to communicate with the primary receiver unit 404 for receiving, among others, the measured analyte level. Alternatively, the primary receiver unit 404 may be configured to integrate an infusion device therein so that the primary receiver unit 404 is configured to administer insulin (or other appropriate drug) therapy to patients, for example, for administering and modifying basal profiles, as well as for determining appropriate boluses for administration based on, among others, the detected analyte levels received from the data processing unit 402. An infusion device may be an external device or an internal device (wholly implantable in a user).

In certain embodiments, the data processing terminal 405, which may include an insulin pump, may be configured to receive the analyte signals from the data processing unit 402, and thus, incorporate the functions of the primary receiver unit 404 including data processing for managing the patient's insulin therapy and analyte monitoring. In certain embodiments, the communication link 403 as well as one or more of the other communication interfaces shown in FIG. 4, may use one or more of: an RF communication protocol, an infrared communication protocol, a Bluetooth enabled communication protocol, an 802.11x wireless communication protocol, or an equivalent wireless communication protocol which would allow secure, wireless communication of several units (for example, per HIPPA requirements), while avoiding potential data collision and interference.

Figure 5:
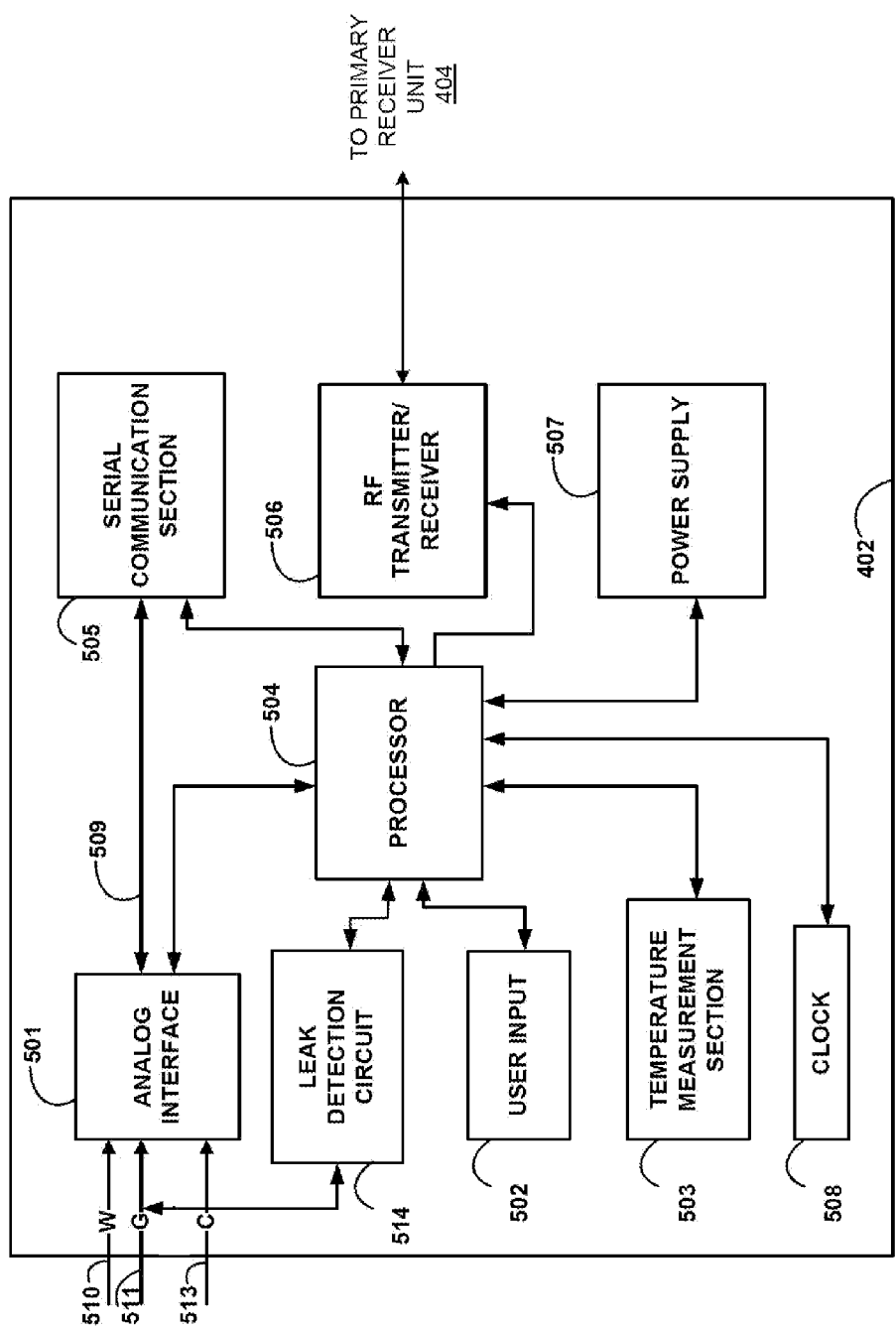
FIG. 5 shows a block diagram of an embodiment of the transmitter unit of the data monitoring and management system of FIG. 4.

FIG. 5 shows a block diagram of an embodiment of a data processing unit of the data monitoring and detection system shown in FIG. 4. User input and/or interface components may optionally be included or a data processing unit may be free of user input and/or interface components. In certain embodiments, one or more application-specific integrated circuits (ASIC) may be used to implement one or more functions or routins associated with the operations of the data processing unit (and/or receiver unit) using for example one or more state machines and buffers.

As can be seen in the embodiment of FIG. 5, the sensor unit 401 (FIG. 4) includes three contacts, two of which are electrodes—working electrode (W) 510, and counter electrode (C) 513, each operatively coupled to the analog interface 501 of the data processing unit 402. This embodiment also shows optional guard contact (G) 511. Fewer or greater electrodes may be employed. For example, there may be more than one working electrode and/or counter electrode, etc.

Figure 6:
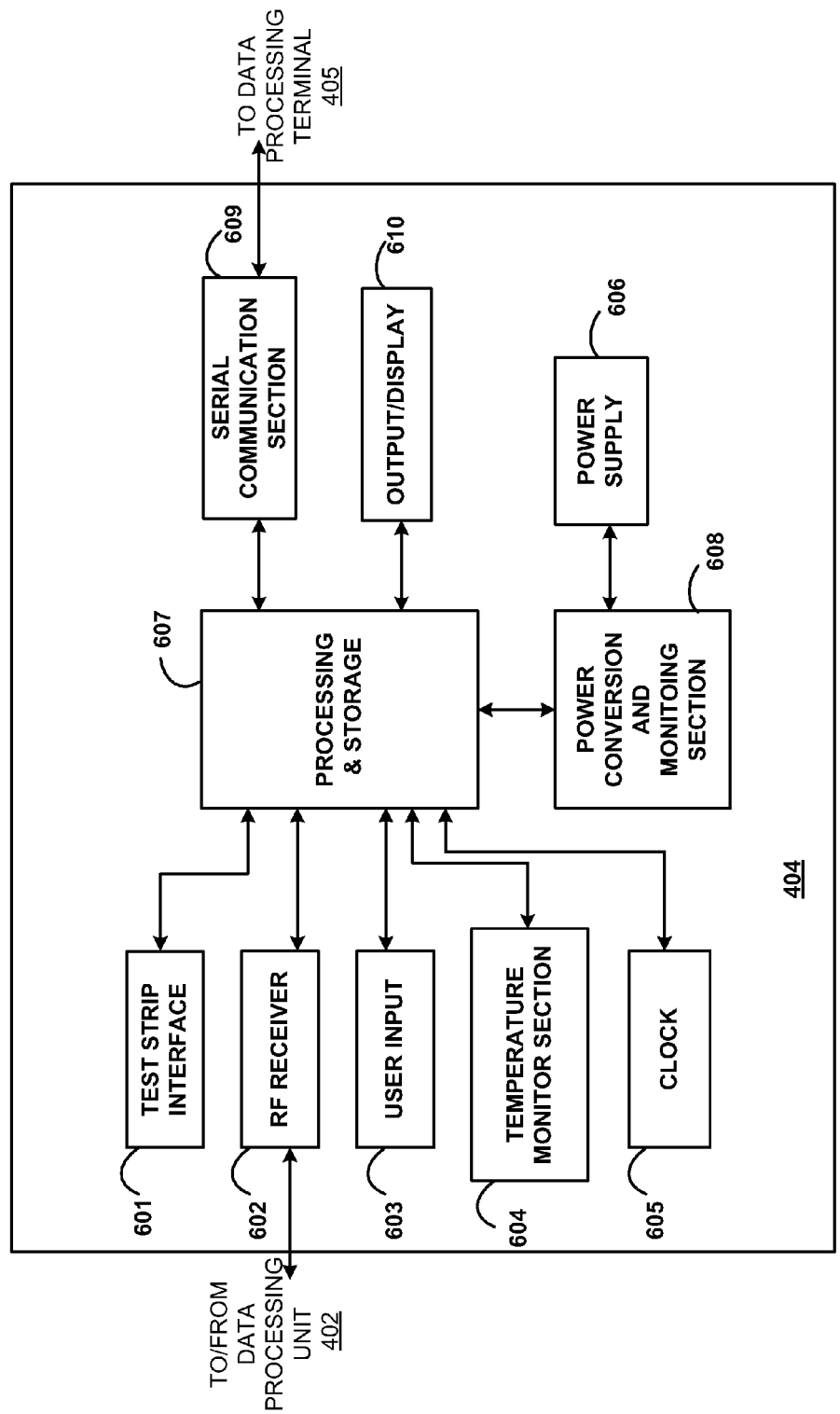
FIG. 6 shows a block diagram of an embodiment of the receiver/monitor unit of the data monitoring and management system of FIG. 4.

FIG. 6 is a block diagram of an embodiment of a receiver/monitor unit such as the primary receiver unit 404 of the data monitoring and management system shown in FIG. 4. The primary receiver unit 404 includes one or more of: a blood glucose test strip interface 601, an RF receiver 602, an input 603, a temperature detection section 604, and a clock 605, each of which is operatively coupled to a processing and storage section 607. The primary receiver unit 404 also includes a power supply 606 operatively coupled to a power conversion and monitoring section 608. Further, the power conversion and monitoring section 608 is also coupled to the receiver processor 607. Moreover, also shown are a receiver serial communication section 609, and an output 610, each operatively coupled to the processing and storage unit 607. The receiver may include user input and/or interface components or may be free of user input and/or interface components.

In certain embodiments, the test strip interface 601 includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 610 of the primary receiver unit 404. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. FreeStyle® blood glucose test strips from Abbott Diabetes Care, Inc. Glucose information obtained by the in vitro glucose testing device may be used for a variety of purposes, computations, etc. For example, the information may be used to calibrate sensor 401, confirm results of the sensor 401 to increase the confidence thereof (e.g., in instances in which information obtained by sensor 401 is employed in therapy related decisions), etc.

In further embodiments, the data processing unit 402 and/or the primary receiver unit 404 and/or the secondary receiver unit 405, and/or the data processing terminal/ infusion section 405 may be configured to receive the blood glucose value wirelessly over a communication link from, for example, a blood glucose meter. In further embodiments, a user manipulating or using the analyte monitoring system 400 (FIG. 4) may manually input the blood glucose value using, for example, a user interface (for example, a keyboard, keypad, voice commands, and the like) incorporated in the one or more of the data processing unit 402, the primary receiver unit 404, secondary receiver unit 405, or the data processing terminal/infusion section 405.

Additional detailed descriptions are provided in U.S. Pat. Nos. 5,262,035; 5,264,104; 5,262,305; 5,320,715; 5,593, 852; 6,175,752; 6,650,471; 6,746, 582, and in application Ser. No. 10/745,878 filed Dec. 26, 2003 entitled "Continuous Glucose Monitoring System and Methods of Use", each of which is incorporated herein by reference.

FIG. 7 schematically shows an embodiment of an analyte sensor in accordance with the embodiments of the invention. This sensor embodiment includes electrodes 701 and 703 on a base 704. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching, and the like. Materials include, but are not limited to, any one or more of aluminum, carbon (including graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 700 may include a portion positionable above a surface of the skin 710, and a portion positioned below the skin. In such embodiments, the external portion may include contacts (connected to respective electrodes of the second portion by traces) to connect to another device also external to the user such as a transmitter unit. While the embodiment of FIG. 7 shows two electrodes side-by-side on the same surface of base 704, other configurations are contemplated, e.g., greater electrodes, some or all electrodes on different surfaces of the base or present on another base, some or all electrodes stacked together, electrodes of differing materials and dimensions, etc.

FIG. 8A shows a perspective view of an embodiment of an electrochemical analyte sensor 800 having a first portion (which in this embodiment may be characterized as a major portion) positionable above a surface of the skin 810, and a second portion (which in this embodiment may be characterized as a minor portion) that includes an insertion tip 830 positionable below the skin, e.g., penetrating through the skin and into, e.g., the subcutaneous space 820, in contact with the user's biofluid such as interstitial fluid. Contact portions of a working electrode 801 and a counter electrode 803 are positioned on the portion of the sensor 800 situated above the skin surface 810. Working electrode 801 and a counter electrode 803 are shown at the second section and particularly at the insertion tip 830. Traces may be provided from the electrode at the tip to the contact, as shown in FIG. 8A. It is to be understood that greater or fewer electrodes may be provided on a sensor. For example, a sensor may include more than one working electrodes.

FIG. 8B shows a cross sectional view of a portion of the sensor 800 of FIG. 8A. The electrodes 801 and 803 of the sensor 800 as well as the substrate and the dielectric layers are provided in a layered configuration or construction. For example, as shown in FIG. 8B, in one aspect, the sensor 800 (such as the sensor unit 401 FIG. 4), includes a substrate layer 804, and a first conducting layer 801 such as carbon, gold, etc., disposed on at least a portion of the substrate layer 804, and which may provide the working electrode. Also shown disposed on at least a portion of the first conducting layer 801 is a sensing layer 808.

A first insulation layer such as a first dielectric layer 805 is disposed or layered on at least a portion of the first conducting layer 801. A second conducting layer 803 may provide the counter electrode 803. It may be disposed on at least a portion of the first insulation layer 805. Finally, a second insulation layer may be disposed or layered on at least a portion of the second conducting layer 803. In this manner, the sensor 800 may be layered such that at least a portion of each of the conducting layers is separated by a respective insulation layer (for example, a dielectric layer). The embodiment of FIGS. 8A and 8B show the layers having different lengths. Some or all of the layers may have the same or different lengths and/or widths.

In certain embodiments, some or all of the electrodes 801, 803 may be provided on the same side of the substrate 804 in the layered construction as described above, or alternatively, may be provided in a co-planar manner such that two or more electrodes may be positioned on the same plane (e.g., side-by side (e.g., parallel) or angled relative to each other) on the substrate 804. For example, co-planar electrodes may include a suitable spacing there between and/or include dielectric material or insulation material disposed between the conducting layers/electrodes. Furthermore, in certain embodiments one or more of the electrodes 801, 803 may be disposed on opposing sides of the substrate 804. In such embodiments, contact pads may be one the same or different sides of the substrate. For example, an electrode may be on a first side and its respective contact may be on a second side, e.g., a trace connecting the electrode and the contact may traverse through the substrate.

As noted above, analyte sensors may include an analyte-responsive enzyme to provide a sensing component or sensing layer. Some analytes, such as oxygen, can be directly electrooxidized or electroreduced on a sensor, and more specifically at least on a working electrode of a sensor. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing layer (see for example sensing layer 808 of FIG. 8B) proximate to or on a surface of a working electrode. In many embodiments, a sensing layer is formed near or on only a small portion of at least a working electrode.

The sensing layer includes one or more components constructed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both. The sensing layer and the working electrode also function as the anode of the power generating component of the self-powered analyte sensor, thereby providing the dual-function of power generation and analyte level detection.

A variety of different sensing layer configurations may be used. In certain embodiments, the sensing layer is deposited on the conductive material of a working electrode. The sensing layer may extend beyond the conductive material of the working electrode. In some cases, the sensing layer may also extend over other electrodes.

A sensing layer that is in direct contact with the working electrode may contain an electron transfer agent to transfer electrons directly or indirectly between the analyte and the working electrode, and/or a catalyst to facilitate a reaction of the analyte. For example, a glucose, lactate, or oxygen electrode may be formed having a sensing layer which contains a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing layer is not deposited directly on the working electrode. Instead, the sensing layer 808 may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer and/or an interferent eliminating layer and/or a biocompatible layer.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic.

Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine etc. Additional examples include those described in U.S. Pat. No. 6,736,957 and U.S. Patent Publication Nos. 2004/0079653 and 2006/0201805, the disclosures of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

The sensing layer may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensing layer functions at a gentle oxidizing potential, e.g., a potential of about +40 mV vs. Ag/AgCl. This sensing layer uses, for example, an osmium (Os)-based mediator constructed for low potential operation and includes a plasticizer. Accordingly, in certain embodiments the sensing element is a redox active component that includes (1) Osmium-based mediator molecules that include (bidente) ligands, and (2) glucose oxidase enzyme molecules. These two constituents are combined together with a cross-linker.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating, etc.

In certain embodiments, a mass transport limiting layer is a membrane composed of crosslinked polymers containing heterocyclic nitrogen groups, such as polymers of polyvinylpyridine and polyvinylimidazole. In some embodiments, a plasticizer is combined with the mass transport limiting layer or membrane. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. In certain embodiments, the membrane formulation further includes a plasticizer. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction.

The substrate may be formed using a variety of non-conducting materials, including, for example, polymeric or plastic materials and ceramic materials. Suitable materials for a particular sensor may be determined, at least in part, based on the desired use of the sensor and properties of the materials.

In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors are made using a relatively rigid substrate to, for example, provide structural support against bending or breaking. Examples of rigid materials that may be used as the substrate include poorly conducting ceramics, such as aluminum oxide and silicon dioxide. One advantage of an implantable sensor having a rigid substrate is that the sensor may have a sharp point and/or a sharp edge to aid in implantation of a sensor without an additional insertion device.

It will be appreciated that for many sensors and sensor applications, both rigid and flexible sensors will operate adequately. The flexibility of the sensor may also be controlled and varied along a continuum by changing, for example, the composition and/or thickness of the substrate.

In addition to considerations regarding flexibility, it is often desirable that implantable sensors should have a substrate which is physiologically harmless, for example, a substrate approved by a regulatory agency or private institution for in vivo use.

The sensor may include optional features to facilitate insertion of an implantable sensor. For example, the sensor may be pointed at the tip to ease insertion. In addition, the sensor may include a barb which assists in anchoring the sensor within the tissue of the patient during operation of the sensor. However, the barb is typically small enough so that little damage is caused to the subcutaneous tissue when the sensor is removed for replacement.

An implantable sensor may also, optionally, have an anticlotting agent disposed on a portion of the substrate which is implanted into a patient. This anticlotting agent may reduce or eliminate the clotting of blood or other body fluid around the sensor, particularly after insertion of the sensor. Blood clots may foul the sensor or irreproducibly reduce the amount of analyte which diffuses into the sensor. Examples of useful anticlotting agents include heparin and tissue plasminogen activator (TPA), as well as other known anticlotting agents.

The anticlotting agent may be applied to at least a portion of that part of the sensor that is to be implanted. The anticlotting agent may be applied, for example, by bath, spraying, brushing, or dipping. The anticlotting agent is allowed to dry on the sensor. The anticlotting agent may be immobilized on the surface of the sensor or it may be allowed to diffuse away from the sensor surface. Typically, the quantities of anticlotting agent disposed on the sensor are far below the amounts typically used for treatment of medical conditions involving blood clots and, therefore, have only a limited, localized effect.

Insertion Device

An insertion device can be used to subcutaneously insert the self-powered analyte sensor into the patient. The insertion device is typically formed using structurally rigid materials, such as metal or rigid plastic. Exemplary materials include stainless steel and ABS (acrylonitrile-butadiene-styrene) plastic. In some embodiments, the insertion device is pointed and/or sharp at the tip to facilitate penetration of the skin of the patient. A sharp, thin insertion device may reduce pain felt by the patient upon insertion of the self-powered analyte sensor. In other embodiments, the tip of the insertion device has other shapes, including a blunt or flat shape. These embodiments may be particularly useful when the insertion device does not penetrate the skin but rather serves as a structural support for the sensor as the sensor is pushed into the skin.

Sensor Control Unit

The sensor control unit can be integrated in the sensor, part or all of which is subcutaneously implanted or it can be configured to be placed on the skin of a patient. The sensor control unit is optionally formed in a shape that is comfortable to the patient and which may permit concealment, for example, under a patient's clothing. The thigh, leg, upper arm, shoulder, or abdomen are convenient parts of the patient's body for placement of the sensor control unit to maintain concealment. However, the sensor control unit may be positioned on other portions of the patient's body. One embodiment of the sensor control unit has a thin, oval shape to enhance concealment. However, other shapes and sizes may be used.

The particular profile, as well as the height, width, length, weight, and volume of the sensor control unit may vary and depends, at least in part, on the components and associated functions included in the sensor control unit. In general, the sensor control unit includes a housing typically formed as a single integral unit that rests on the skin of the patient. The housing typically contains most or all of the electronic components of the sensor control unit.

The housing of the sensor control unit may be formed using a variety of materials, including, for example, plastic and polymeric materials, particularly rigid thermoplastics and engineering thermoplastics. Suitable materials include, for example, polyvinyl chloride, polyethylene, polypropylene, polystyrene, ABS polymers, and copolymers thereof. The housing of the sensor control unit may be formed using a variety of techniques including, for example, injection molding, compression molding, casting, and other molding methods. Hollow or recessed regions may be formed in the housing of the sensor control unit. The electronic components of the sensor control unit and/or other items, including a battery or a speaker for an audible alarm, may be placed in the hollow or recessed areas.

The sensor control unit is typically attached to the skin of the patient, for example, by adhering the sensor control unit directly to the skin of the patient with an adhesive provided on at least a portion of the housing of the sensor control unit which contacts the skin or by suturing the sensor control unit to the skin through suture openings in the sensor control unit.

When positioned on the skin of a patient, the sensor and the electronic components within the sensor control unit are coupled via conductive contacts. The one or more working electrodes, counter electrode, and optional temperature probe are attached to individual conductive contacts. For example, the conductive contacts are provided on the interior of the sensor control unit. Other embodiments of the sensor control unit have the conductive contacts disposed on the exterior of the housing. The placement of the conductive contacts is such that they are in contact with the contact pads on the sensor when the sensor is properly positioned within the sensor control unit.

Sensor Control Unit Electronics

The sensor control unit also typically includes at least a portion of the electronic components that measure the sensor current and the analyte monitoring device system. The electronic components of the sensor control unit typically include a power supply for operating the sensor control unit, a sensor circuit for obtaining signals from the sensor, a measurement circuit that converts sensor signals to a desired format, and a processing circuit that, at minimum, obtains signals from the sensor circuit and/or measurement circuit and provides the signals to an optional transmitter. In some embodiments, the processing circuit may also partially or completely evaluate the signals from the sensor and convey the resulting data to the optional transmitter and/or activate an optional alarm system if the analyte level exceeds a threshold. The processing circuit often includes digital logic circuitry.

The sensor control unit may optionally contain a transmitter for transmitting the sensor signals or processed data from the processing circuit to a receiver/display unit; a data storage unit for temporarily or permanently storing data from the processing circuit; a temperature probe circuit for receiving signals from and operating a temperature probe; a reference voltage generator for providing a reference voltage for comparison with sensor-generated signals; and/or a watchdog circuit that monitors the operation of the electronic components in the sensor control unit.

Moreover, the sensor control unit may also include digital and/or analog components utilizing semiconductor devices, including transistors. To operate these semiconductor devices, the sensor control unit may include other components including, for example, a bias control generator to correctly bias analog and digital semiconductor devices, an oscillator to provide a clock signal, and a digital logic and timing component to provide timing signals and logic operations for the digital components of the circuit.

As an example of the operation of these components, the sensor circuit and the optional temperature probe circuit provide raw signals from the sensor to the measurement circuit. The measurement circuit converts the raw signals to a desired format, using for example, a current-to-voltage converter, current-to-frequency converter, and/or a binary counter or other indicator that produces a signal proportional to the absolute value of the raw signal. This may be used, for example, to convert the raw signal to a format that can be used by digital logic circuits. The processing circuit may then, optionally, evaluate the data and provide commands to operate the electronics.

Calibration

Sensors may be configured to require no system calibration or no user calibration. For example, a sensor may be factory calibrated and need not require further calibrating. In certain embodiments, calibration may be required, but may be done without user intervention, i.e., may be automatic. In those embodiments in which calibration by the user is required, the calibration may be according to a predetermined schedule or may be dynamic, i.e., the time for which may be determined by the system on a real-time basis according to various factors, including, but not limited to, glucose concentration and/or temperature and/or rate of change of glucose, etc.

In addition to a transmitter, an optional receiver may be included in the sensor control unit. In some cases, the transmitter is a transceiver, operating as both a transmitter and a receiver. The receiver may be used to receive calibration data for the sensor. The calibration data may be used by the processing circuit to correct signals from the sensor. This calibration data may be transmitted by the receiver/display unit or from some other source such as a control unit in a doctor's office. In addition, the optional receiver may be used to receive a signal from the receiver/display units to direct the transmitter, for example, to change frequencies or frequency bands, to activate or deactivate the optional alarm system and/or to direct the transmitter to transmit at a higher rate.

Calibration data may be obtained in a variety of ways. For instance, the calibration data may simply be factory-determined calibration measurements which can be input into the sensor control unit using the receiver or may alternatively be stored in a calibration data storage unit within the sensor control unit itself (in which case a receiver may not be needed). The calibration data storage unit may be, for example, a readable or readable/writeable memory circuit.

Calibration may be accomplished using an in vitro test strip (or other reference), e.g., a small sample test strip such as a test strip that requires less than about 1 microliter of sample (for example FreeStyle® blood glucose monitoring test strips from Abbott Diabetes Care). For example, test strips that require less than about 1 nanoliter of sample may be used. In certain embodiments, a sensor may be calibrated using only one sample of body fluid per calibration event. For example, a user need only lance a body part one time to obtain sample for a calibration event (e.g., for a test strip), or may lance more than one time within a short period of time if an insufficient volume of sample is firstly obtained. Embodiments include obtaining and using multiple samples of body fluid for a given calibration event, where glucose values of each sample are substantially similar. Data obtained from a given calibration event may be used independently to calibrate or combined with data obtained from previous calibration events, e.g., averaged including weighted averaged, etc., to calibrate. In certain embodiments, a system need only be calibrated once by a user, where recalibration of the system is not required.

Alternative or additional calibration data may be provided based on tests performed by a doctor or some other professional or by the patient. For example, it is common for diabetic individuals to determine their own blood glucose concentration using commercially available testing kits. The results of this test is input into the sensor control unit either directly, if an appropriate input device (e.g., a keypad, an optical signal receiver, or a port for connection to a keypad or computer) is incorporated in the sensor control unit, or indirectly by inputting the calibration data into the receiver/display unit and transmitting the calibration data to the sensor control unit.

Other methods of independently determining analyte levels may also be used to obtain calibration data. This type of calibration data may supplant or supplement factory-determined calibration values.

In some embodiments of the invention, calibration data may be required at periodic intervals, for example, every eight hours, once a day, or once a week, to confirm that accurate analyte levels are being reported. Calibration may also be required each time a new sensor is implanted or if the sensor exceeds a threshold minimum or maximum value or if the rate of change in the sensor signal exceeds a threshold value. In some cases, it may be necessary to wait a period of time after the implantation of the sensor before calibrating to allow the sensor to achieve equilibrium. In some embodiments, the sensor is calibrated only after it has been inserted. In other embodiments, no calibration of the sensor is needed.

Analyte Monitoring Device

In some embodiments of the invention, the analyte monitoring device includes a sensor control unit and a self-powered analyte sensor. In some embodiments, the processing circuit of the sensor control unit is able to determine a level of the analyte and activate an alarm system if the analyte level exceeds a threshold. The sensor control unit, in these embodiments, has an alarm system and may also include a display, such as an LCD or LED display.

A threshold value is exceeded if the datapoint has a value that is beyond the threshold value in a direction indicating a particular condition. For example, a datapoint which correlates to a glucose level of 200 mg/dL exceeds a threshold value for hyperglycemia of 180 mg/dL, because the datapoint indicates that the patient has entered a hyperglycemic state. As another example, a datapoint which correlates to a glucose level of 65 mg/dL exceeds a threshold value for hypoglycemia of 70 mg/dL because the datapoint indicates that the patient is hypoglycemic as defined by the threshold value. However, a datapoint which correlates to a glucose level of 75 mg/dL would not exceed the same threshold value for hypoglycemia because the datapoint does not indicate that particular condition as defined by the chosen threshold value.

An alarm may also be activated if the sensor readings indicate a value that is beyond a measurement range of the sensor. For glucose, the physiologically relevant measurement range is typically about 30 to 500 mg/dL, including about 40-300 mg/dL and about 50-250 mg/dL, of glucose in the interstitial fluid.

The alarm system may also, or alternatively, be activated when the rate of change or acceleration of the rate of change in analyte level increase or decrease reaches or exceeds a threshold rate or acceleration. For example, in the case of a subcutaneous glucose monitor, the alarm system might be activated if the rate of change in glucose concentration exceeds a threshold value which might indicate that a hyperglycemic or hypoglycemic condition is likely to occur.

A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

Drug Delivery System

The subject invention also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Each of the various references, presentations, publications, provisional and/or non-provisional U.S. patent applications, U.S. patents, non-U.S. patent applications, and/or non-U.S. patents that have been identified herein, is incorporated herein in its entirety by this reference.

Other aspects, advantages, and modifications within the scope of the invention will be apparent to those skilled in the art to which the invention pertains. Various modifications, processes, as well as numerous structures to which the embodiments of the invention may be applicable will be readily apparent to those of skill in the art to which the invention is directed upon review of the specification. Various aspects and features of the invention may have been explained or described in relation to understandings, beliefs, theories, underlying assumptions, and/or working or prophetic examples, although it will be understood that the invention is not bound to any particular understanding, belief, theory, underlying assumption, and/or working or prophetic example. Although various aspects and features of the invention may have been described largely with respect to applications, or more specifically, medical applications, involving diabetic humans, it will be understood that such aspects and features also relate to any of a variety of applications involving non-diabetic humans and any and all other animals. Further, although various aspects and features of the invention may have been described largely with respect to applications involving partially implanted sensors, such as transcutaneous or subcutaneous sensors, it will be understood that such aspects and features also relate to any of a variety of sensors that are suitable for use in connection with the body of an animal or a human, such as those suitable for use as fully implanted in the body of an animal or a human. Finally, although the various aspects and features of the invention have been described with respect to various embodiments and specific examples herein, all of which may be made or carried out conventionally, it will be understood that the invention is entitled to protection within the full scope of the appended claims.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Current/Time and Calibration Curves for Self-Powered Analyte Sensors Compared to a Standard Three Electrode Potentiostat-Powered Analyte Sensor A self-powered glucose sensor was constructed using either a redox polymer or platinum-carbon cloth (Pt—C) as an oxygen reducing species on the counter electrode and glucose oxidase (GOx) as glucose oxidizing species on the working electrode, which also acts as the analyte responsive enzyme of the glucose sensor. Fabrication of the self-powered analyte sensors is described below.

Working electrode (glucose oxidizing anode): 30 nL of a solution including 8.2 mg/mL GOx, 6.8 mg/mL redox polymer (a poly(vinylpyridine) derivative containing covalently bound Os complexes), and 5 mg/mL PEG 400 crosslinker, all dissolved in 10 mM HEPES, was deposited on the working electrode of a continuous glucose monitor sensor, such as a Navigator® electrode, to form an active area of about 0.1 mm². This electrode was overlaid with the flux-limiting membrane, approximately 50 micron thick coating of the membrane polymer (a poly(vinylpyridine) derivative) crosslinked with tri-glycidyl glycerol.

Counter electrode (oxygen reducing cathode): 150 nL of a solution including 5.2 mg/mL redox polymer dissolved in PBS, was deposited on the entirety of the working electrode of a continuous glucose monitor sensor, such as a Navigator® electrode, to form an active area of about 0.9 mm². This electrode was overlaid with a flux-limiting membrane, an approximately 50 micron thick coating of the membrane polymer (a poly(vinylpyridine) derivative), crosslinked with tri-glycidyl glycerol.

A 4.67 Mohm resistor was placed between these two electrodes, and the resulting spontaneous current was measured, as the sensor pair was exposed to varying glucose concentrations and at varying time points. The output of this circuit was compared to that from the identical working electrode in 3-electrode mode (paired through a potentiostat with an Ag/AgCl reference and a carbon counter electrode), as well as to the same working electrode paired in self-powered mode with a Pt/carbon counter electrode. The results are shown in FIG. 9 and FIG. 10.

Figure 9:
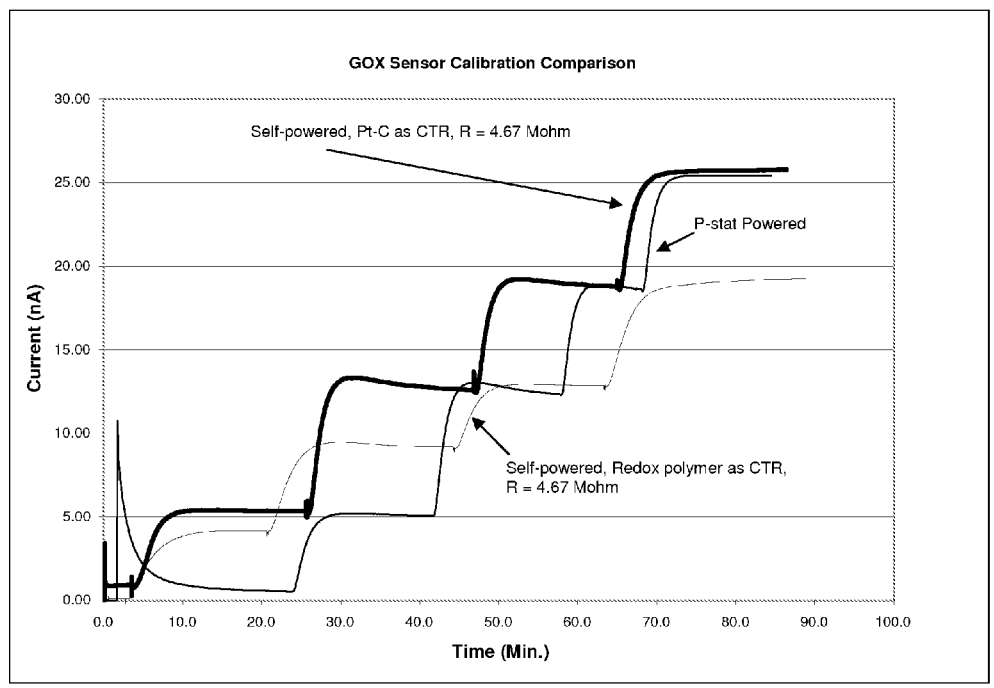
FIG. 9 is a graph showing sensor calibration comparison for three sensors having a wired glucose oxidase (GOX) working electrode: a potentiostat powered analyte sensor control; a self-powered analyte sensor having a platinum-carbon (Pt—C) counter electrode; and a self-powered analyte sensor having a redox polymer counter electrode.

Glucose aliquots were added to produce concentrations of 4, 12, 20, and 28 mM, as evident from the humps in FIG. 9. As shown in FIG. 9, it was observed that the self-powered glucose sensor with a Pt—C counter electrode provided an identical result to a three electrode potentiostat-powered sensor, while the self-powered glucose sensor fabricated with a redox polymer based counter electrode gave a somewhat reduced current response.

Figure 10:
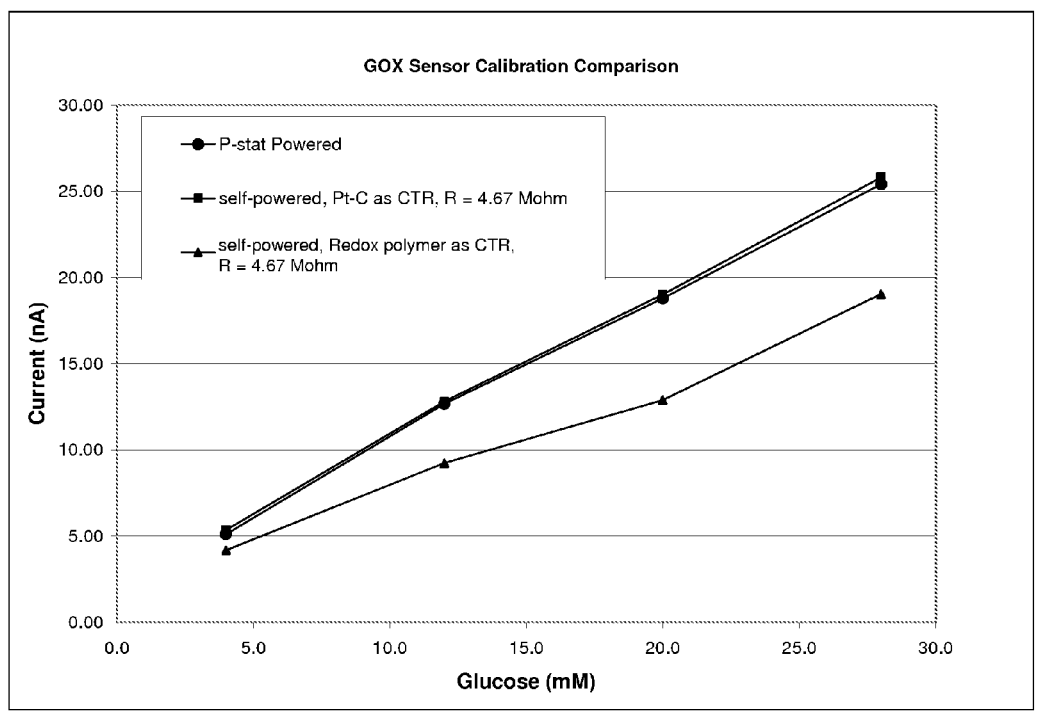
FIG. 10 is a graph showing calibration curves for three sensors having a wired glucose oxidase (GOX) working electrode: a potentiostat powered analyte sensor control (circles); a self-powered analyte sensor having a platinum-carbon (Pt—C) counter electrode (squares); and a self-powered analyte sensor having a redox polymer counter electrode (triangles).

Calibration curves from the data shown in FIG. 9 are provided in FIG. 10. As shown in FIG. 10, the Pt—C counter electrode based self-powered sensor provided equivalent data to the three electrode potentiostat-powered sensor, while the self-powered glucose sensor fabricated with a redox polymer based counter electrode gave a somewhat reduced current response.

Example 2

Intermittent Powering of Self-Powered Analyte Sensor Compared to a Standard Three Electrode Potentiostat-Powered Analyte Sensor For many applications, it is desirable to intermittently address or query a sensor for current values, while leaving the sensor unpowered in the intervening intervals, since this can result in enormous savings in power consumption, and therefore overall size of the analyte sensor. Unfortunately, it is not feasible to intermittently power the current generation of a standard continuous glucose sensors since they have a relatively long response time. This is illustrated in FIG. 11, which shows a comparison of intermittently powering the current generation of a standard continuous glucose sensor (P-stat powered) and self-powered sensor having a Pt—C counter electrode as described in Example 1 (Self-powered, Pt—C as CTR).

Figure 11:
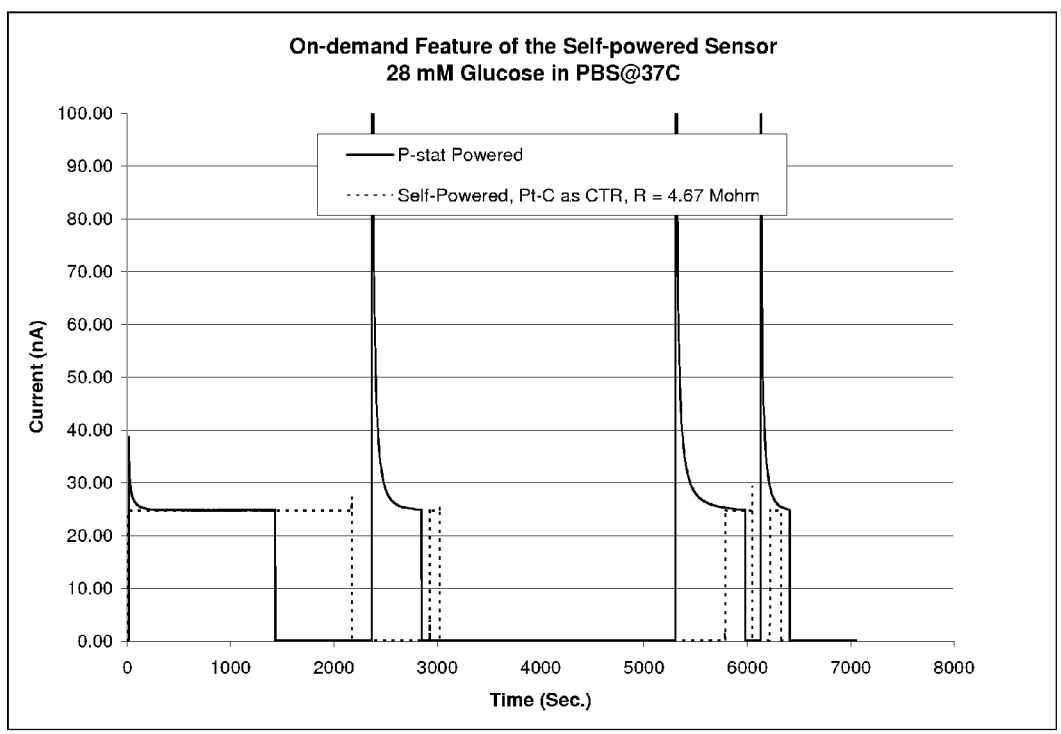
FIG. 11 is a graph showing the equilibration time required for a standard potentiostat powered analyte sensor and a self-powered analyte sensor following disconnection and connection of powered measurement electronics.

As shown in FIG. 11, when a potentiostat powered standard continuous glucose sensor is turned off for 10 minutes, it requires at least 6 minutes to equilibrate when it is turned back on. In addition, when the potentiostat powered standard continuous glucose sensor is turned off for an hour, it requires at least 15 minutes to equilibrate when it is turned back on. However, the self-powered sensor having a Pt—C counter electrode is always "on" even in the absence of any power expenditure. Therefore, as shown in FIG. 11, there is no equilibration time required after the self-powered sensor is reconnected to a current or voltage measuring circuit.

Example 3

Self-Powered Sensor Based on an Oxygen Reducing Enzyme

The oxygen reducing counter electrode of a self-powered sensor can also be constructed of an oxygen reducing enzyme, in addition to the other materials previously discussed, such as Pt, Pt black, and redox polymer. The enzyme, in this case bilirubin oxidase (BOD) can accept electrons directly from oxygen, then transmit them to the counter electrode through a cross-linked redox polymer. Fabrication of the self-powered analyte sensors is described below.

Working electrode (glucose oxidizing anode): 30 nL of a solution including 8.2 mg/mL GOx, 6.8 mg/mL redox polymer (a poly(vinylpyridine) derivative containing covalently bound Os complexes), and 5 mg/mL PEG 400 cross-linker, all dissolved in 10 mM HEPES, was deposited on the working electrode of a continuous glucose sensor, such as a Navigator® sensor, to form an active area of about 0.1 mm$^2$. This electrode was overlaid with a flux-limiting membrane, an approximately 50 micron thick coating of the membrane polymer (a poly(vinylpyridine) derivative) cross-linked with tri-glycidyl glycerol.

Counter electrode (oxygen reducing cathode): 150 nL of a solution including 12.6 mg/mL BOD, 5.2 mg/mL redox polymer, and 5.4 mg/mL PEG 400 cross-linker, all dissolved in PBS, was deposited on the entirety of the working electrode of a second continuous glucose sensor, such as a Navigator® sensor, to form an active area of about 0.9 mm$^2$. This electrode was overlaid with a flux-limiting membrane, an approximately 50 micron thick coating of the membrane polymer (a poly(vinylpyridine) derivative) cross-linked with tri-glycidyl glycerol.

Figure 12:
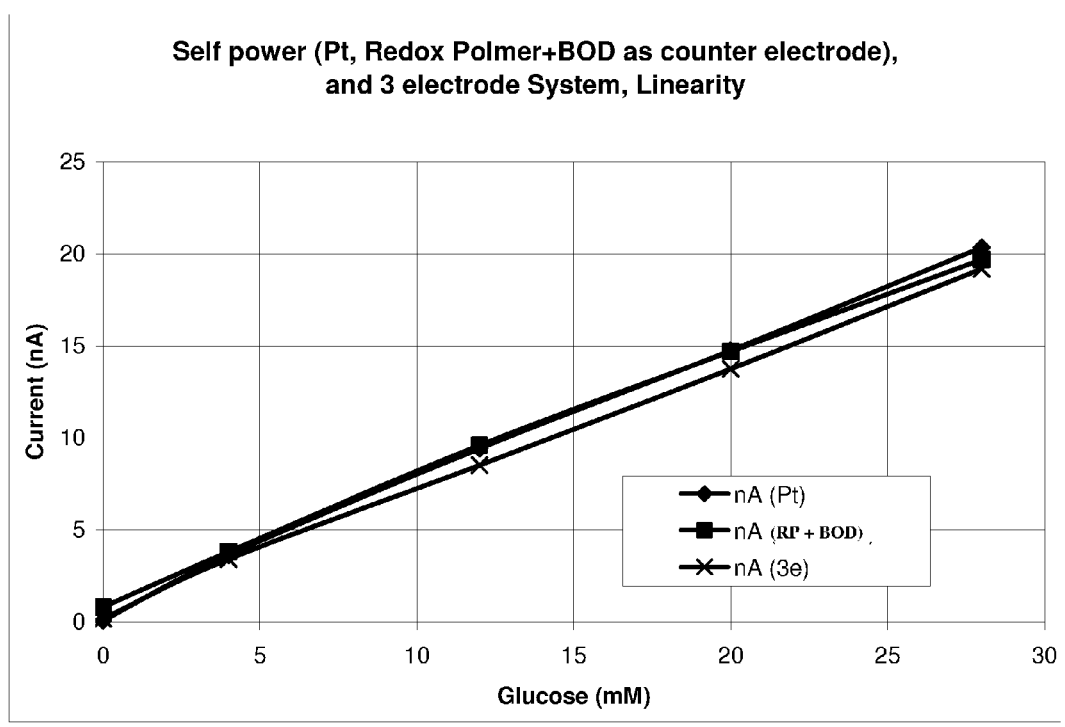
FIG. 12 is a graph showing the calibration curves for three sensors. Data for a potentiostat powered analyte sensor control are represented with crosses, data for a self-powered analyte sensor having a platinum (Pt) counter electrode are represented with diamonds, and data for a self-powered analyte sensor having a redox polymer and bilirubin oxidase (BOD) counter electrode are represented with squares.

A 4.67 Mohm resistor was placed between these two electrodes, and the resulting spontaneous current was measured, as the sensor pair was exposed to varying glucose concentrations. The output of this circuit was compared to that from the identical working electrode in 3-electrode mode (paired through a potentiostat with an Ag/AgCl reference and a carbon counter electrode), as well as to the same working electrode paired in self-powered mode with a Pt/carbon cloth counter electrode. The results are shown in FIG. 12. Note that the currents in all three modes are essentially identical, indicating the redox polymer/BOD counter electrode functions efficiently as an oxygen reducing counter electrode.

Example 4

Self-Powered Sensor Based on FADGDH

A self-powered glucose sensor was constructed using either a redox polymer or platinum (Pt) as an oxygen reducing species on the counter electrode and glucose dehydrogenase complexed with flavin adenine dinucleotide (FADGDH) on the working electrode, which also acts the analyte responsive enzyme for the sensor. Fabrication of the self-powered analyte sensors is described below.

Working electrode (anode): 30 nL of a solution including 8.2 mg/mL FADGDH, 6.8 mg/mL redox polymer (a poly(vinylpyridine) derivative containing covalently bound Os complexes), and 5 mg/mL PEG 400 crosslinker, all dissolved in 10 mM HEPES, was deposited on the working electrode of a continuous glucose monitor sensor, such as a Navigator® electrode, to form an active area of about 0.1 mm$^2$. This electrode was overlaid with the flux-limiting membrane, an approximately 50 micron thick coating of the membrane polymer (a poly(vinylpyridine) derivative) cross-linked with tri-glycidyl glycerol.

Counter electrode (cathode): 150 nL of a solution including 12.6 mg/mL BOD, 5.2 mg/mL redox polymer, and 5.4 mg/mL PEG 400 cross-linker, all dissolved in PBS, was deposited on the entirety of the working electrode of a second continuous glucose sensor, such as a Navigator® sensor, to form an active area of about 0.9 mm$^2$. This electrode was overlaid with a flux-limiting membrane, an approximately 50 micron thick coating of the membrane polymer (a poly(vinylpyridine) derivative) cross-linked with tri-glycidyl glycerol.

Figure 13:
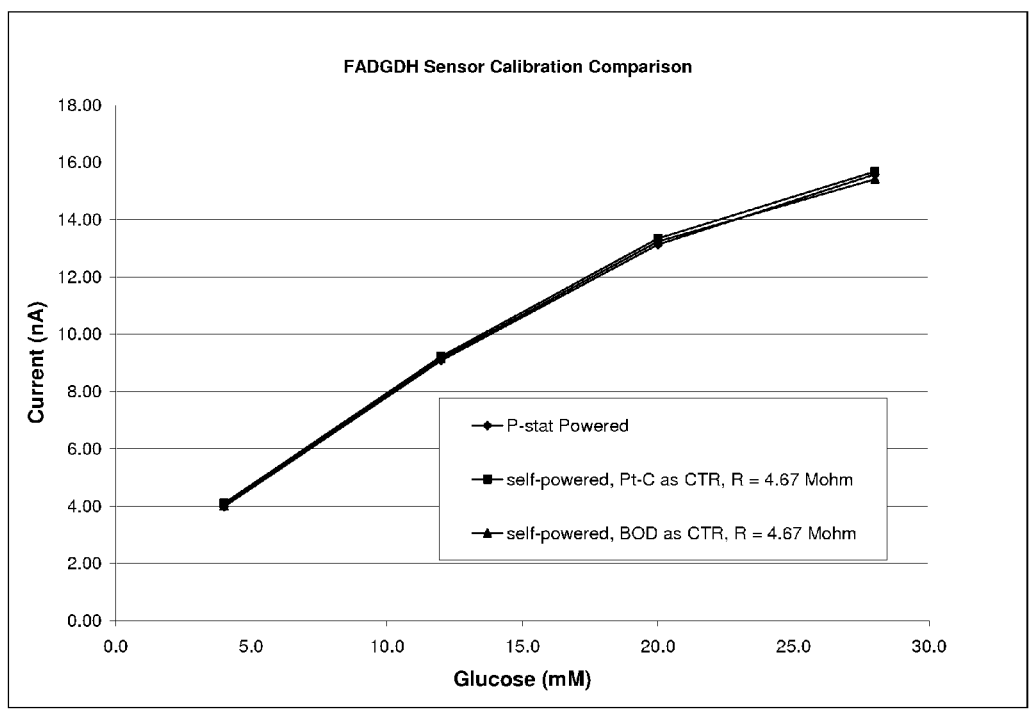
FIG. 13 is a graph showing shows sensor calibration comparison for three sensors having FADGDH based working electrodes. Data for a potentiostat powered analyte sensor control are represented with diamonds, data for a self-powered analyte sensor having a platinum-carbon (Pt—C) counter electrode are represented with squares, and data for a self-powered analyte sensor having bilirubin oxidase (BOD) counter electrode are represented with triangles.

A 4.67 Mohm resistor was placed between these two electrodes, and the resulting spontaneous current was measured, as the sensor pair was exposed to varying glucose concentrations and at varying time points. The output of this circuit was compared to that from the identical working electrode in 3-electrode mode (paired through a potentiostat with an Ag/AgCl reference and a carbon counter electrode), as well as to the same working electrode paired in self-powered mode with a Pt/carbon counter electrode. The results are shown in FIG. 13.

Glucose aliquots were added to produce concentrations of 4, 12, 20, and 28 mM. Calibration curves from the three sensors are shown in FIG. 13. As shown in FIG. 13, the Pt—C based counter electrode based self-powered sensor as well as the BOD based counter electrode based self-powered sensor provided equivalent data to the three electrode potentiostat-powered sensor.

Example 5

Dependence of Self Powered Sensor Response on the Value of R

Figure 14:
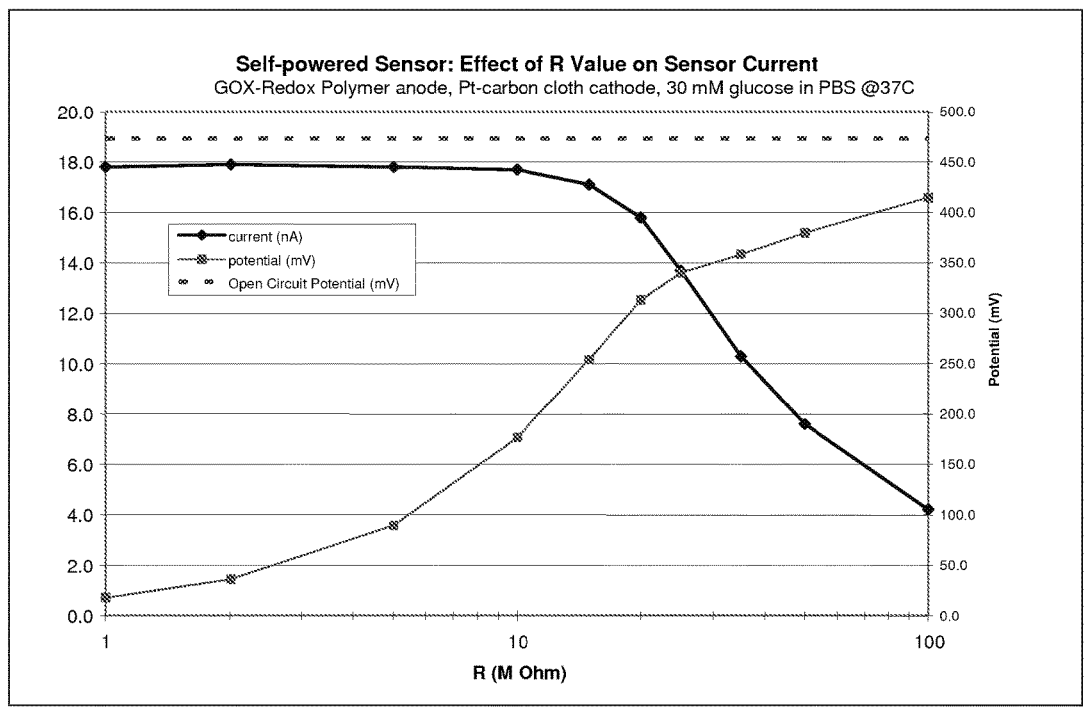
FIG. 14 is a graph showing the effect of R value of the resistance on sensor current.

In order to have a linear response over the concentration range of analytical interest, the correct value of R must be chosen for the resistor which couples together the working electrode and the counter electrode. This is illustrated by the following experiment. A self powered sensor was made from a GOx and redox polymer working electrode, and a Pt-carbon cloth counter electrode, coupled together with a variety of resistors, ranging in resistance from 0 MΩ to 100 MΩ. This sensor was then immersed in 30 mM (540 mg/dL) glucose (the top of the analytical range of interest) in PBS buffer at 37° C., and the resulting spontaneous steady state current was measured for sensors configured with different R values. The results are shown in FIG. 14, with resistance plotted on a logarithmic scale.

Note that the current is essentially independent of resistance for resistance values of 10 MΩ or less, then falls off gradually at higher potentials, as the potential drop becomes a substantial fraction of the open circuit potential. Therefore, to correctly configure the sensor, a value of R should be selected that does not reduce the current output from its maximum value, as illustrated by the plateau in the graph of FIG. 14. In this example, the range of R values from 0 to 10 MΩ is the range of R values for which the sensor output, at an analyte concentration at the top of its physically relevant range, is independent of R. Therefore, an R value of 0 to 10 MΩ should be selected.

Another way to elucidate the correct range for R is in terms of the potential across the resistor. In the sensor described by the graph above, the open circuit potential (shown) is 474 mV. When the potential drop across the resistor is more than half of the open circuit potential, the output of the sensor begins to decline. The potential drop across the resistor is, for example, less than 75% of the open circuit potential, such as less than 50% of the open circuit potential, and less than 25% of the open circuit potential in certain embodiments.

Example 6

In Vivo Self-Powered Glucose Sensor

An in vivo self-powered glucose sensor used for subcutaneous implantation was constructed using the two carbon electrodes on a continuous glucose monitoring electrode of a Navigator® sensor: the working electrode, the counter electrode, and a resistor disposed in between the working electrode and the counter electrode and having an R value of 4.85 Mohm.

Figure 15:
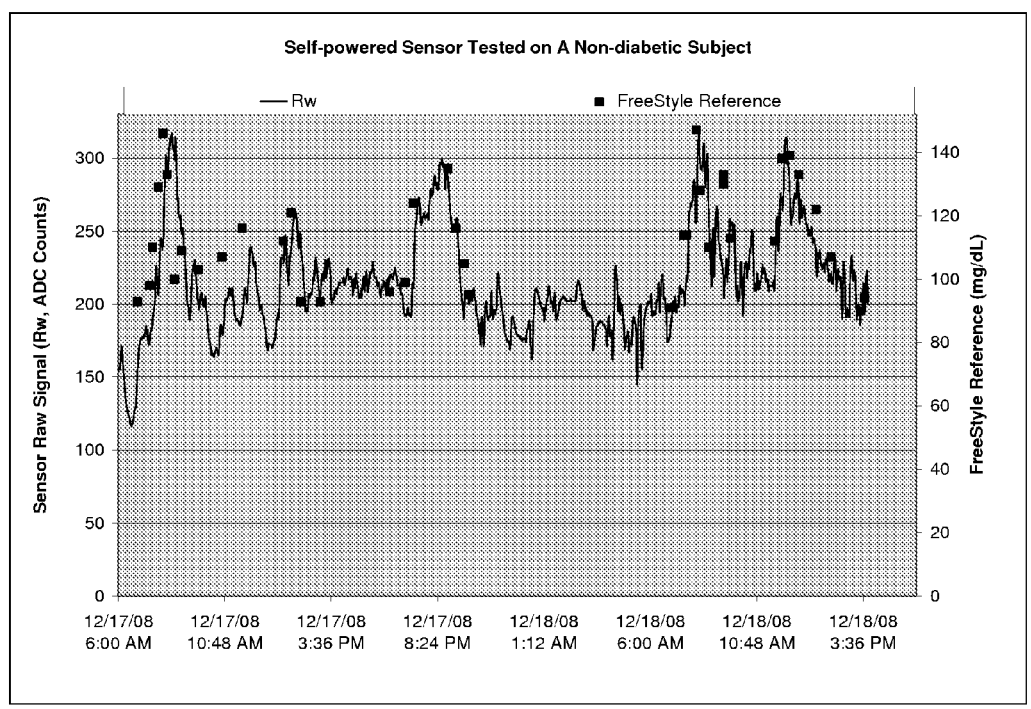
FIG. 15 is a graph showing correlation between an in vivo self powered glucose sensor signal and reference glucose values.

The working electrode was constructed to include redox polymer, glucose oxidase, and cross-linker sensing layer. The counter electrode was constructed to include a layer of platinum catalyst formed by depositing 50 nL 20 mg/ml platinum-carbon black (HiSPEC 8000, Alfa Aesar) suspension in 80% ethanol-20% water. The sensor was then dip-coated with a flux-limiting polymer membrane. After sterilization, the sensor was subcutaneously implanted with an insertion device. The data was collected with a transmitter that sent via radio-frequency, the self-powered sensor current signal to a standard receiver. Reference glucose values were obtained through frequent measurement with FreeStyle® glucose strips. The results in FIG. 15 show good correlation between the in vivo self powered glucose sensor signal and the reference glucose values.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method for monitoring a level of an analyte, the method comprising:
electrooxidizing or electroreducing, on a working electrode within an analyte sensor assembly configured to be positioned onto a skin of a patient, a primary reactant in a presence of an analyte-responsive enzyme;
electroreducing or electrooxidizing a secondary reactant on a counter electrode within the analyte sensor assembly; and
maintaining a current directly proportional to an analyte concentration in an absence of any reference voltage, the current being maintained by a resistor disposed between the working electrode and the counter electrode, wherein the resistor has an R value chosen from within a range of R values for which the current is independent of the R value at an analyte concentration at a top of its physically relevant range.

2. The method of claim 1, further comprising processing, in a data processing unit coupled with the analyte sensor assembly, information from the analyte sensor assembly and associated with the analyte concentration.

3. The method of claim 2, further comprising communicating between a first wireless communication unit and the data processing unit, the first wireless communication unit being coupled to the data processing unit.

4. The method of claim 3, further comprising intermittently receiving an interrogation at the analyte sensor assembly from a second wireless communication unit of a handheld device, the interrogation being received at the first wireless communication unit only upon positioning of the handheld device in close proximity to the analyte sensor assembly.

5. The method of claim 4, wherein the first wireless communication unit is configured to communicate through a first radio-frequency communication protocol.

6. The method of claim 5, wherein the first radio frequency communication protocol is a first radio frequency identification (RFID) communication protocol.

7. The method of claim 1, wherein the analyte sensor assembly comprises an analyte sensor including the working electrode, the counter electrode, and the resistor, and further comprises a radio-frequency powered current measuring circuit coupled to the analyte sensor.

8. The method of claim 7, wherein the radio-frequency powered current measuring circuit is intermittently powered.

9. The method of claim 1, wherein the analyte sensor assembly comprises an analyte sensor including the working electrode, the counter electrode, and the resistor, and further comprises an inductively powered current measuring circuit coupled to the analyte sensor.

10. The method of claim 1, further comprising storing data associated with information from the analyte sensor assembly for a period of time.

11. The method of claim 1, wherein the analyte-responsive enzyme is a glucose-responsive enzyme.

12. The method of claim 1, wherein the working electrode further comprises a redox mediator covalently or ionically associated with a polymeric moiety.

13. The method of claim 12, wherein the analyte responsive enzyme is covalently or ionically associated with the polymeric moiety.

14. The method of claim 12, wherein the redox mediator comprises a transition metal complex, ferricyanide, phenanthroline quinone, or ferrocene.

15. The method of claim 1, wherein the working electrode is configured to electrooxidize the primary reactant in the presence of the analyte-responsive enzyme and the counter electrode is configured to electroreduce the secondary reactant.

16. The method of claim 1, wherein the working electrode is configured to electroreduce the primary reactant in the presence of the analyte-responsive enzyme and the counter electrode is configured to electrooxidize the secondary reactant.

17. The method of claim 1, wherein the R value is such that a potential drop across the resistor, at the analyte concentration at the top of its physically relevant range, is less than 75% of an open circuit potential.

18. The method of claim 1, wherein the primary reactant is glucose.

19. The method of claim 1, wherein the R value is such that a potential drop across the resistor, at the analyte concentration at the top of its physically relevant range, is less than 50% of an open circuit potential.

20. The method of claim 1, wherein the R value is such that a potential drop across the resistor, at the analyte concentration at the top of its physically relevant range, is less than 25% of an open circuit potential.

21. An analyte sensor assembly configured to be positioned onto a skin of a patient and to monitor a level of an analyte, the analyte sensor assembly comprising:
a working electrode configured to electrooxidize or electroreduce a primary reactant in a presence of an analyte-responsive enzyme;
a counter electrode configured to electroreduce or electrooxidize a secondary reactant; and
a resistor connected between the working electrode and the counter electrode, the resistor being configured to maintain a current directly proportional to an analyte concentration in an absence of any reference voltage, wherein the resistor has an R value chosen from within a range of R values for which the current is independent of the R value at an analyte concentration at a top of its physically relevant range.

22. The analyte sensor assembly of claim 21, wherein the R value is such that a potential drop across the resistor, at the analyte concentration at the top of its physically relevant range, is less than 75% of an open circuit potential.

23. The analyte sensor assembly of claim 21, wherein the R value is such that a potential drop across the resistor, at the analyte concentration at the top of its physically relevant range, is less than 50% of an open circuit potential.

24. The analyte sensor assembly of claim 21, wherein the R value is such that a potential drop across the resistor, at the analyte concentration at the top of its physically relevant range, is less than 25% of an open circuit potential.

* * * * *